United States Patent [19]

Marconi et al.

[11] 3,986,928

[45] Oct. 19, 1976

[54] ANTIBIOTIC A-32390 AND PROCESS FOR PREPARATION THEREOF

[75] Inventors: Gary G. Marconi; Marvin M. Hoehn, both of Indianapolis, Ind.

[73] Assignee: Eli Lilly and Company, Indianapolis, Ind.

[22] Filed: Feb. 19, 1976

[21] Appl. No.: 659,606

Related U.S. Application Data

[62] Division of Ser. No. 597,112, July 18, 1975.

[52] U.S. Cl. .................................................. 195/81
[51] Int. Cl.² ........................................... C12D 9/00
[58] Field of Search ....................................... 195/81

[56] References Cited
UNITED STATES PATENTS 3,932,219   1/1976   Michel et al. ........................ 195/81

OTHER PUBLICATIONS

Chemical Abstracts, vol. 65, 15,826 b, 1972.

*Primary Examiner*—A. Louis Monacell
*Assistant Examiner*—Robert J. Warden
*Attorney, Agent, or Firm*—Nancy J. Harrison; Everet F. Smith

[57] ABSTRACT

Antibiotic A-32390 complex, comprising factor A and other structurally related factors, is produced by cultivation of Pyrenochaeta sp. NRRL 5786 under submerged aerobic conditions, and isolated by extraction of the broth. Individual A-32390 factor A is separated by chromatography. The A-32390 complex, individual factor A and acyl ester derivatives of factor A inhibit dopamine-β-hydroxylase and have antifungal, antibacterial, and hypotensive activity.

3 Claims, 2 Drawing Figures

INFRARED ABSORPTION SPECTRUM OF ANTIBIOTIC A-32390 FACTOR A

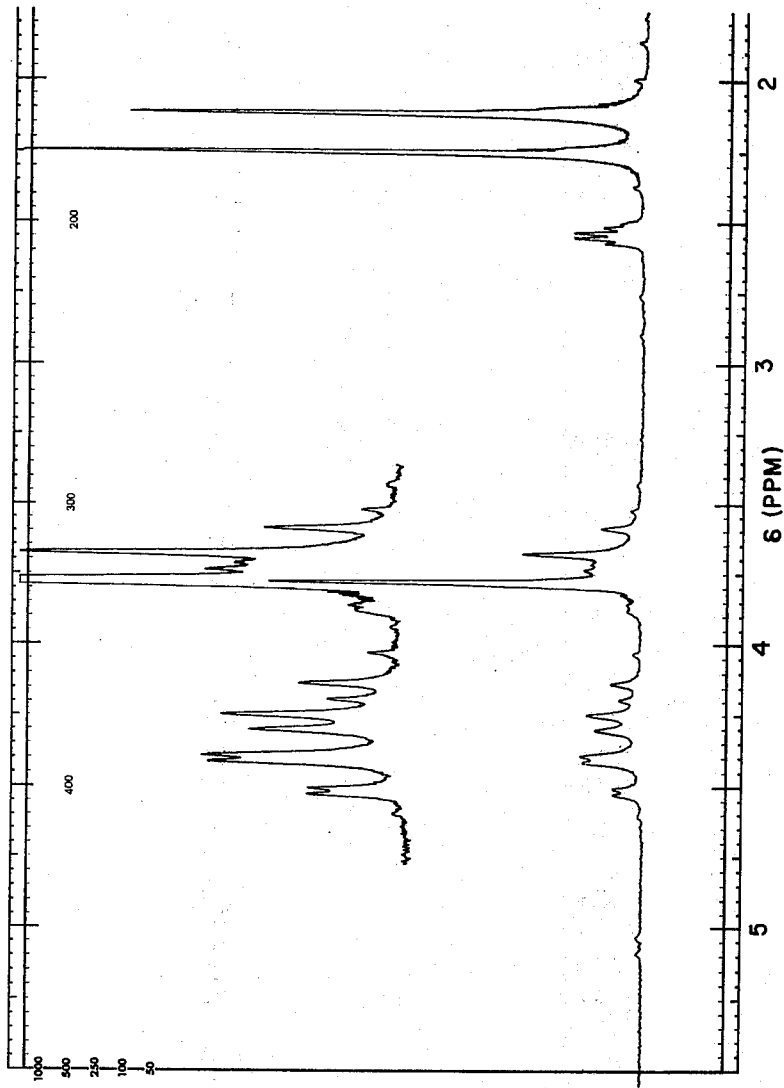

ANTIBIOTIC A-32390 AND PROCESS FOR PREPARATION THEREOF

This is a division of application Ser. No. 597,112, filed July 18, 1975.

SUMMARY OF THE INVENTION

This invention relates to antibiotic substances. In particular, it relates to an antibiotic complex comprising a group of acyclic polyhydric alcohol antibiotics. This invention further relates to the method of producing this antibiotic complex by culturing a novel strain of the organism Pyrenochaeta sp. NRRL 5786.

The term "antibiotic complex" as used in the fermentation art and in this specification refers to a mixture of co-produced individual antibiotic factors. As will be recognized by those familiar with antibiotic production by fermentation, the ratio of individual factors produced in an antibiotic complex will vary, depending on the fermentation conditions used.

The antibiotic complex of this invention is arbitrarily designated herein as antibiotic A-32390. The most abundant individual factor is designated as antibiotic A-32390 factor A. This invention also relates to the tetra-($C_2$—$C_4$)-acyl ester derivatives of individual A-32390 factor A.

The A-32390 antibiotic complex is produced by culturing a novel strain of Pyrenochaeta sp. NRRL 5786 under submerged aerobic fermentation conditions until a level of antibiotic activity is produced. The A-32390 antibiotic complex is recovered from the fermentation medium by extracting the broth with a polar organic solvent and concentrating the extract to give antibiotic A-32390 complex as an impure crystalline solid. Antibiotic A-32390 factor A is separated from other A-32390 factors and is isolated as an individual compound by the use of well-known techniques such as column chromatography and thin-layer chromatography.

The A-32390 antibiotic complex and individual factor A inhibit the growth of organisms which are pathogenic to animal and plant life. The A-32390 antibiotics are especially valuable because of their activity against fungi such as Candida albicans. In addition, the A-32390 antibiotic complex, individual A-32390 factor A, and the tetra-($C_2$—$C_4$)-acyl ester derivatives of A-32390 factor A inhibit the enzyme dopamine-$\beta$-hydroxylase and are hypotensive agents.

DESCRIPTION OF THE DRAWINGS

The infrared absorption spectrum of antibiotic A-32390 factor A in a mineral-oil mull is presented in the drawings as FIG. 1. The nuclear magnetic resonance spectrum of antibiotic A-32390 factor A in dimethyl sulfoxide-$d_6$/$D_2O$ is presented in the drawings as FIG. 2.

DETAILED DESCRIPTION OF THE INVENTION

Figure 1:
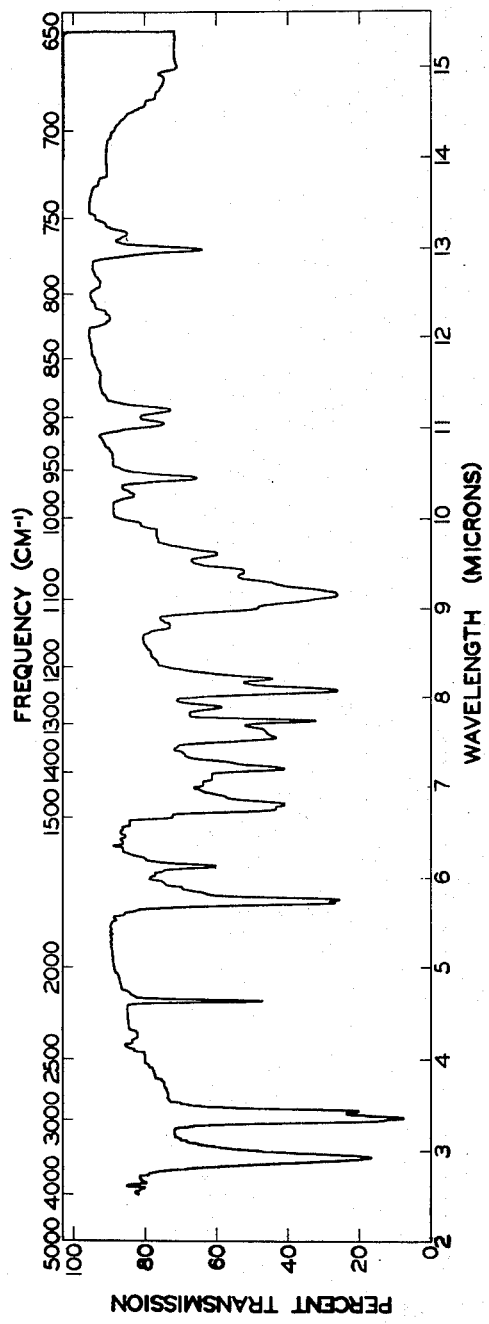

The A-32390 antibiotic complex of this invention is comprised of at least four factors designated as factors A, B, C, and D. The antibiotic factors thus far separated appear to be structurally related to each other and exhibit the chemical, physical and spectral characteristics of polyhydric alcohols. These antibiotic factors are coproduced during fermentation and are obtained as a complex. The factors are separated, and factor A is isolated as an individual compound as hereinafter described. The partially pure A-32390 antibiotic complex is a gray powder which is soluble in dimethylformamide, dimethylacetamide and dimethyl sulfoxide; is slightly soluble in lower alcohols, acetone, ethyl acetate and chloroform; but is substantially insoluble in water, benzene, hexane, diethyl ether and carbon tetrachloride.

Factors A, B, C, and D are separated from the A-32390 antibiotic complex by chromatography. For example, thin-layer chromatography on silica gel G (Merck, F-254), using a chloroform-methanol (9:1) solvent system separates A-32390 factors A, B, C, and D. Using Sarcina lutea ATCC 3241 as a detection organism, the $R_f$ values of the A-32390 factors in this system are:

| Factor | $R_f$ |
| --- | --- |
| A | 0.32 |
| B | 0.23 |
| C | 0.15 |
| D | 0.05 |

The following paragraphs describe the physical and spectral properties of A-32390 factor A.

Antibiotic A-32390 factor A is a white crystalline compound which melts at about 162° C. The empirical formula proposed for factor A is $C_{18}H_{24}N_2O_8$. Elemental analysis of factor A gave the following percentage composition: carbon, 54.63%; hydrogen, 6.03%; nitrogen, 7.38%. Oxygen by difference would be 31.96%. This corresponds to a calculated percentage composition: carbon, 54.6; hydrogen, 6.06; nitrogen, 7.07; oxygen, 32.27. The molecular weight of factor A, as determined by mass spectrometry, is 396. The observed specific rotation of factor A, $[\alpha]_D^{25}$, is +17°(c=1, dimethylformamide).

The infrared absorption spectrum of antibiotic A-32390 factor A in mineral-oil mull is shown in FIG. 1 of the accompanying drawings. The distinguishable bands in the infrared spectrum are as follows [w=weak; m=medium; s=strong]: 2.92(s), 4.64(m), 5.73(m-s), 5.76(m-s), 6.14(w-m), 7.54(m), 7.74(m), 7.89(w), 8.08(m-s), 8.21(w-m), 8.80(w), 9.15(m-s), 9.40(w), 9.60(w), 10.25(w), 10.45(w-m), 11.05(w), 11.20(w), 12.22(w), 13.00(w-m) and 13.16(w) microns.

The ultraviolet absorption spectrum of antibiotic A-32390 factor A in 95% ethanol shows an absorption maximum, $\lambda$max, at 230 nm ($\epsilon$27,900).

The nuclear magnetic resonance spectrum of antibiotic A-32390 factor A in dimethyl sulfoxide is shown in FIG. 2 of the accompanying drawings. The spectrum has the following characteristics: $\delta$2.11 (s), 2.24 (s), 3.61 (dd, J = 9, 7 Hz), 3.77 (dddd, J = 9, 6, 5.5, 2 Hz), 4.21 (dd, J = 11, 6 Hz), 4.45 (dd, J = 11, 2 Hz), 4.42 (exchangeable d, J = 7 Hz) and 4.91 ppm (exchangeable d, J = 5.5 Hz).

Antibiotic A-32390 factor A, crystallized from acetone, has the following characteristic X-ray powder diffraction pattern (chromium radiation, 2.2896 $\lambda$, vanadium filter, d=interplanar spacing in angstroms, I/I$_1$= relative intensity):

| d | I/I$_1$ |
| --- | --- |
| 18.75 | 100 |
| 9.33 | 50 |
| 7.48 | 10 |
| 6.93 | 10 |
| 6.46 | 70 |
| 6.11 | 40 |

| d | I/I₁ |
|---|---|
| 5.17 | 70 |
| 4.77 | 30 |
| 4.54 | 30 |
| 4.27 | 30 |
| 3.76 | 10 |
| 3.60 | 70 |
| 3.46 | 60 |
| 3.33 | 05 |
| 3.25 | 30 |
| 3.02 | 05 |
| 2.48 | 05 |
| 2.37 | 05 |

Antibiotic A-32390 factor A is soluble in dimethylformamide, dimethylacetamide and dimethyl sulfoxide; is slightly soluble in acetone, ethyl acetate and chloroform; but is substantially insoluble in water, benzene, hexane, diethyl ether and carbon tetrachloride. A-32390 factor A is also slightly soluble, but is unstable, in lower alcohols.

Antibiotic A-32390 factor A has been determined to have the following structure:

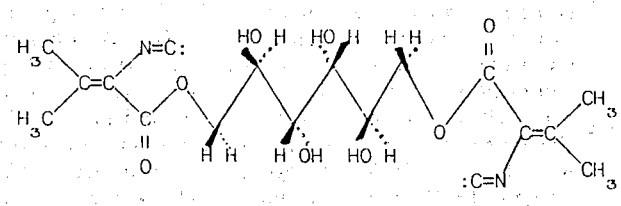

which structure is designated 1,6-di-O-(2-isocyano-3-methylcrotonyl)-D-mannitol. In the above formula the isocyano groups are depicted as —N≡C: groups.

Antibiotic A-32390 factor A has four hydroxyl groups capable of esterification. The tetra-($C_2$—$C_4$)-acyl ester derivatives of A-32390 factor A are prepared from factor A by standard esterification procedures.

Antibiotic A-32390 factor A and the tetra-($C_2$—$C_4$)-acyl ester derivatives of A-32390 factor A can be represented by the structural formula:

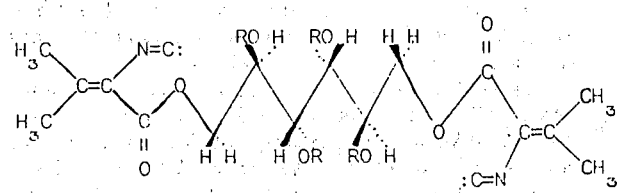

wherein all R's are the same and are selected from the group consisting of hydrogen, acetyl, propionyl and butyryl.

The organism which produces the A-32390 antibiotics was isolated by a serial dilution procedure from a subtropical soil sample. This organism has been taxonomically characterized as a new strain of the genus Pyrenochaeta which is in the order Sphaeropsidales of the Deuteromycetes (Fungi Imperfecti).

CULTURAL CHARACTERISTICS

Czapek's-Solution Agar

At 26° C the culture grows poorly and forms a few scattered pycnidia.

Malt-Extract Agar

After incubation for 7 days at 26° C, abundant aerial hyphae form with relatively few and widely scattered pycnidia.

Potato-Dextrose Agar

After incubation for seven days at 26° C, numerous frequently clustered pycnidia and short aerial hyphae are produced. Both the upper and lower surfaces of the colony are brownish-black. Colony diameter is 35–40 mm after eight days with little additional growth thereafter.

MORPHOLOGICAL CHARACTERISTICS

Pycnidia are superficial, cespitose, membranous to subcarbonaceous, black, with open and slightly rostrate ostiole, setose, globose to subglobose, 135 × 155 μ to 235 × 275 μ, averaging 169 × 195 μ.

Setae are rigid, brown to black, smooth, tapered with rounded tips, 3–5 septate, and have enlarged basal ends which form a dark brown ring around a nearly circular ostiole (whirled effect). Infrequently, setae which lack the enlarged basal end occur scattered over the pycnidial surface. Setae are 63 × 2 μ to 112 × 6.2 μ near the base (average 81.25 × 6.2 μ).

Unicellular spores are discharge through the ostiole in a mucoid mass. The spores are hyaline, cylindrical (a few are allentoid) with rounded ends, and bigluttulate. Spores measure 7 to 9 μ long and 2.8 μ wide (average 8.4 × 2.8 μ). They are elaborated from phialides which arise from the pycnidial wall. These phialides are tapered from base to apex (2.8 to 1.8 μ) and are from 18.2 to 29.4 μ long (average 22 μ).

A culture of the A-32390-producing organism has been deposited with the permanent culture collection of the U.S. Department of Agriculture, Agricultural Research Service, Northern Regional Research Laboratory, Peoria, Illinois 61604, where it has been deposited without restriction as to availability and has been accorded the accession number, NRRL 5786.

As is the case with other organisms, the characteristics of the Pyrenochaeta sp. NRRL 5786 A-32390-producing strain are subject to variation. For example, artificial variants and mutants of the NRRL 5786 strain may be obtained by various known mutagens such as ultraviolet rays, X-rays, high-frequency waves, radioactive rays and chemicals. All natural and artificial variants and mutants which belong to this Pyrenochaeta species and produce the A-32390 antibiotics may be used in this invention.

The culture medium employed to produce the A-32390 antibiotic complex can be any one of a number of media since the A-32390-producing organism is capable of utilizing energy from a variety of nutrient sources. Thus, for example, a variety of carbohydrates can be included in the culture medium to supply the carbon requirements for the organism. Likewise, various sources of nitrogen, such as amino acids, distiller's extracts and the like can be employed in the A-32390 medium. For reasons of economy in production, optimal yield, and ease of isolation of the antibiotic, certain culture media are preferred. For example, a preferred carbohydrate source in the fermentation is glucose, although fructose, mannose, maltose, dextrin and sucrose may also be used.

The addition of certain crotonic acid derivatives, such as 2-cyano-3-methylcrotonic acid, ethyl 2-cyano-3-methylcrotonate, and methoxyethyl 2-cyano-3-methylcrotonate, to the culture media appears to give enhanced yields of the A-32390 antibiotic complex.

Ethyl alcohol is another agent which may be added to the culture medium to enhance the yield of A-32390 antibiotics.

Preferred sources of nitrogen are peptones, soybean meal, amino acid mixtures and the like. As is common in the production of antibiotics in general, nutrient inorganic salts can be incorporated in the culture medium for the production of A-32390 antibiotics. Such inorganic nutrients are the customary salts capable of yielding sodium, potassium, ammonium, calcium, phosphate, chloride, carbonate, and like ions.

Essential elements necessary for the growth and development of the A-32390-producing organism should also be included in the culture medium. Such essential elements are usually required in only trace amounts. These trace elements commonly occur as impurities in the other constituents of the medium in amounts sufficient to meet the requirements of growth for the A-32390-producing organism.

The strain of the organism employed to produce the A-32390 antibiotics is capable of growing under a variety of conditions. For example, the organism will grow in a variety of media in which the initial pH varies rather extensively. However, it has been found desirable to initiate the fermentation in a medium at a pH between about 6 and about 8 and preferably between about 6 and 7. Commonly, during the growth of the organism, the pH of the medium will decrease slightly from the initial levels. The final pH of the culture medium is dependent at least in part on such factors as the initial pH of the medium, the buffers present therein, and the length of time the organism is allowed to grow.

The A-32390-producing organism of the present invention is capable of growing and producing antibiotic activity on various types of media. The organism can be grown on agar slants, in shake flasks, or in medium- or large-scale fermentation tanks. For large-scale production of these antibiotics, submerged aerobic fermentation conditions are preferable. For the preparation of relatively small quantities of the A-32390 antibiotic complex, shake-flask culture can be employed.

In carrying out submerged aerobic fermentation to produce the A-32390 antibiotics, the organism is at first grown on agar-slant cultures or, preferably, in submerged aerobic culture in a glycerol-lactose medium, the latter being stored in the vapor phase of liquid nitrogen. The fungus is transferred to a vegetative medium to insure a rapid growth of the organism on a small scale. This inoculated vegetative medium is allowed to grow until a viable culture of the organism is obtained with which to inoculate a larger tank. The use of a vegetative medium as an intermediate stage in the production of the antibiotic is preferable to direct inoculation of a large tank. Inoculation of a large tank by means of a vegetative medium provides more rapid organism growth than is obtained by direct inoculation by means of spores.

The A-32390-producing organism grows at temperatures ranging from about 18 to about 37° C. Optimal antibiotic production appears to occur at temperatures from about 22 to about 28° C.

As is customary in aerobic, submerged culture processes, sterile air is blown through the culture medium during the fermentation process. For efficient organism growth and antibiotic production, the volume of air employed is preferably in excess of about 0.1 volumes of air per volume of culture medium per minute (v/v/m). In submerged aerobic fermentation of the A-32390 antibiotics, optimal yields are obtained when the volume of air employed is at least 0.3 v/v/m.

In general, when submerged aerobic fermentation conditions or shake-flask culture conditions are employed, maximum production of the A-32390 antibiotics occurs between about 3 to about 6 days after the inoculation of the culture medium. Maximum production of A-32390 antibiotics in large-scale fermentation tanks under submerged aerobic conditions occurs at about 96 hours.

The course of the fermentation can be followed by assaying the fermentation medium from time to time against an organism susceptible to the A-32390 antibiotics. One such organism which can be employed is *Sarcina lutea* ATCC 9341.

Following production under submerged aerobic fermentation conditions, the A-32390 antibiotics can be recovered from the fermentation broth by methods employed in the fermentation art. The filtered broth contains the major portion of the A-32390 antibiotics produced during fermentation. The mycelium contains a relatively small amount of the A-32390 antibiotics produced.

Under the conditions employed thus far, the organism described previously and designated as Pyrenochaeta sp. NRRL 5786 produces factor A as the predominant factor. In general, factor A is present in amounts from about 60 to about 95 percent of the total recovered A-32390 antibiotics.

The A-32390 antibiotics are recovered from the fermentation medium as an antibiotic complex. Since the majority of antibiotic activity is associated with the broth, a preferred method of recovery is filtration of the fermentation medium. The filtered fermentation broth is then extracted with a suitable organic solvent. The resulting extract is treated with a drying agent and then is concentrated to a small volume to give the A-32390 antibiotic complex as a crude semicrystalline solid precipitate.

Solvents which are esters, such as ethyl acetate, amyl acetate and isoamyl acetate, are suitable solvents with which to extract the filtered broth. Ethyl acetate is a preferred solvent for extraction.

An alternate method for recovering the A-32390 antibiotic complex is by adsorption onto a macroreticular resin such as Amberlite XAD-2 or XAD-4 (Rohm and Haas). Acetone is a particularly useful eluting solvent for this procedure.

Alternatively, the whole fermentation broth can be extracted with a suitable water-immiscible solvent, such as ethyl acetate; and this extract can be concentrated as above to obtain the A-32390 antibiotic complex.

The A-32390 antibiotic complex can be further purified by methods such as fractional crystallization or chromatography over a suitable adsorbent. Suitable adsorbents include silica gel, magnesium silicate, and the like.

Antibiotic A-32390 factor A is separated and isolated as an individual compound most readily by a combination of fractional crystallization and chromatographic methods. For example, factor A is isolated from the A-32390 antibiotic complex by chromatography over silica gel and subsequent crystallization from acetone. Minor factors B, C, and D are present in the mother liquor after crystallization and separation of factor A. The minor factors may be further separated by, for example, preparative thin-layer chromatography.

The following examples are provided in order to more fully illustrate the methods and procedures of the present invention.

EXAMPLE 1

A. Slant Culture of A-32390

A culture of Pyrenochaeta sp. 5786 was prepared on an agar slant having the following composition:

| Ingredient | Amount |
| --- | --- |
| Agar (Meer, washed three times) | 20.00 g |
| Dextrose | 20.00 g |
| Peptone | 5.00 g |
| $KH_2PO_4$ | .50 g |
| $MgSO_4.7H_2O$ | .02 g |
| $FeSO_4.7H_2O$ | .01 g |
| Deionized water | q.s. 1 liter |

The pH of the medium is adjusted to pH 6.2 by the addition of sodium hydroxide. The pH of the medium after sterilization is approximately 5.4.

The slant was inoculated with Pyrenochaeta sp. NRRL 5786, and the inoculated slant was incubated at 25° C for 7 days.

B. Shake-Flask Fermentation of A-32390

One-half of the mature slant culture was scraped with a sterile needle and used to inoculate 50 ml of a vegetative medium having the following composition:

| Ingredient | Amount |
| --- | --- |
| Glucose | 25 g |
| Edible molasses | 36 g |
| Corn-steep liquor | 6 g |
| Malt extract | 10 g |
| N-Z Case* | 10 g |
| Czapek's Mineral Stock** | 2 ml |
| Deionized water | q.s. 1100 ml |

*Enzymatic digest of casein, Sheffield Chemical Co., Norwich, New York
**Czapek's Mineral Stock has the following composition:

| Ingredient | Amount |
| --- | --- |
| $FeSO_4.7H_2O$ (Dissolved in 2 ml conc. HCl) | 2 g |
| KCl | 100 g |
| $MgSO_4.7H_2O$ | 100 g |
| Deionized water | q.s. to 1 liter |

The inoculated vegetative medium, in a 250-ml Erlenmeyer flask, was incubated for 2 days at 25° C on a shaker rotating through an arc 2 inches in diameter at 250 rpm.

This incubated vegetative medium may be used directly to inoculate the second-stage vegetative medium or, alternatively, it can be preserved in storage by maintaining the culture in the vapor phase of liquid nitrogen. The culture is prepared for later use in multiple small vials as follows: In each vial is placed 2 ml of incubated vegetative medium and 2 ml of a glycerol-lactose solution having the following composition:

| Ingredient | Amount |
| --- | --- |
| Glycerol | 200 g |
| Lactose | 100 g |
| Deionized water | q.s. 1 liter |

The prepared suspensions are store in the vapor phase of liquid nitrogen.

A stored suspension (1 ml) thus prepared was used to inoculate 50 ml of a first-stage vegetative medium having the same composition earlier-described for the vegetative medium. Two replicate inoculated flask (250 ml) were incubated for 2 days at 25° C on shakers rotating through arcs of 2 inches at 250 rpm.

In order to provide a larger volume of inoculum, 10 ml of the incubated first-stage vegetative medium was used to inoculate 200 ml of a second-stage vegetative medium also having the same composition as that of the vegetative medium. Four replicate inoculated flasks (1-liter volume) were incubated for one day at 25° C on shakers rotating through arcs of 2 inches at 250 rpm.

C. Tank Fermentation of A-32390

The incubated second-stage vegetative medium (800 ml) was used to inoculate 100 liters of sterile production medium having the following composition:

| Ingredient | Amount |
| --- | --- |
| Sucrose | 30.00 g/l. |
| Glucose | 15.00 g/l. |
| Cottonseed flour | 5.00 g/l. |
| KCl | 0.50 g/l. |
| $K_2HPO_4$ | 0.20 g/l. |
| $FeSO_4.7H_2O$ | 0.01 g/l. |
| $NaNO_3$ | 0.50 g/l. |
| $MgSO_4.7H_2O$ | 0.50 g/l. |
| Antifoam Agents | 0.70 g/l. |
| Czapek's Mineral Stock | 2.00 ml/l. |
| Ethanol (95%) | 14.00 ml/l. |
| Deionized water | q.s. 1 liter |

This medium had an unadjusted pH of 6.6. Adjustment to pH 7.3 was made by the addition of approximately 10 ml of 10 N sodium hydroxide before sterilization. The medium had a ph of 6.4 after sterilization at 120° C for 30 minutes at 16 to 18 pounds pressure.

In a 165-liter fermentation tank, the inoculated production medium was allowed to ferment for 4 days at a temperature of 25° C. During this time, the fermentation medium was aerated with sterile air at the rate of 0.25 v/v/m. The medium was stirred with a conventional agitator at 200 rpm.

EXAMPLE 2

Separation of the A-32390 Antibiotic Complex

Fermentation broth (100 liters), prepared as described in Example 1 was filtered, using 3–5 percent of a filter aid (Hyflo Supercel). The broth filtrate (about pH 7.0) thus obtained was extracted with ethyl acetate (two 60-liter portions). The combined ethyl acetate extracts were evaporated under vacuum to a volume of one liter. This solution was cooled (5° C) for 24 hours. The semicrystalline precipitate which formed was separated by filtration, washed with cold ethyl acetate (50 ml), and dried under vacuum to give the A-32390 antibiotic complex.

EXAMPLE 3

Isolation of A-32390 Factor A

A-32390 antibiotic complex (5 g), prepared as described in Example 2, was slurried in benzene (100 ml). This slurry was applied to a 3.7- × 90-cm silica gel (Matheson, grade 62) column prepared in benzene. The column was eluted successively with benzene (2 liters), 1:1 benzene-ethyl acetate (3 liters), and ethyl acetate (500 ml). Further elution with ethyl acetate (12.5 liters) separated the fractions containing A-32390 factor A. These fractions were combined and evaporated to dryness under vacuum. The residue thus obtained was dissolved in hot acetone (50 ml). A-32390 factor A crystallized upon cooling. Factor A was separated by filtration, washed with cold acetone (10 ml) and dried under vacuum (yield 1.5 g).

EXAMPLE 4

Preparation of A-32390 Factor A Tetraacetate

Antibiotic A-32390 factor A (206 mg), prepared as described in Example 3, was dissolved in dry distilled pyridine (5 ml). Acetic anhydride (2.5 ml) was added to this solution. The resulting solution was allowed to stand overnight at room temperature and then was concentrated under vacuum to a residue. This residue was dissolved in a water-acetone mixture, and the resulting solution was again evaporated under vacuum to a residue. The residue was repreatedly redissolved in chloroform and re-evaporated under vacuum until the resulting residue had no detectable pyridine odor.

The final residue, dissolved in 2 ml of chloroform, was placed on a silica-gel column (Grace, grade 62, 1.5 × 30 cm). The column was eluted with chloroform at a rate of about 3 ml/min. Twenty-five 15-ml fractions were collected. Active fractions (7–11) were combined and concentrated under vacuum to a syrupy residue. This residue was redissolved and re-evaporated from diethyl ether and then was dried under vacuum to give 268 mg of A-32390 factor A tetraacetate as a syrup (91% yield).

EXAMPLE 5

Antibiotic A-32390 factor A tetrapropionate derivative was prepared by reacting A-32390 factor A and propionic anhydride in pyridine using the procedures described in Example 4.

EXAMPLE 6

Antibiotic A-32390 factor A tetrabutyrate derivative was prepared by reacting A-32390 factor A and n-butyric anhydride in pyridine, using the procedures described in Example 4.

During the following discussions of utility, the antibiotic A-32390 complex, individual factor A, and the tetra-$(C_2-C_4)$-acyl ester derivatives of factor A of the present invention will, for the sake of brevity, be called "A-32390 antibiotic compounds."

The A-32390 antibiotic compounds inhibit the growth of microorganisms that are pathogenic to animals and plants. The in vitro activities of individual A-32390 factor A and various tetraacyl ester derivatives of factor A against representative organisms are summarized in Table I. Activity is measured as the diameter of the zone of inhibition effected by the test compound when present at a level of 1 mg/ml.

TABLE I

| Organism | Factor A | Zone Diameters | | |
| --- | --- | --- | --- | --- |
| | | Tetra-acetate | Tetra-propionate | Tetra-butyrate |
| Staphylococcus aureus | 30 | 20 | 12 | trace |
| Bacillus subtilis | 30 | 20 | 11 | — |
| Sarcina lutea | 28 | 24 | 12 | 9 |
| Mycobacterium avium | 26 | 10 | — | — |
| Saccharomyces pastorianus | 24 | 24 | 22 | 10 |
| Neurospora crassa | 20 | 18 | 16 | 9 |
| Candida tropicalis | 19 | 15 | 14 | — |
| Fusarium moniliforme | — | 28 | 17 | — |
| Trichophyton mentagrophytes | — | 22 | 11 | — |
| Escherichia coli | 30 | 27 | 19 | — |

There is a great need for improved antifungal agents, especially for agents which are active systemically. Only one systemic drug of choice, Amphotericin B, is presently available for the treatment of a large number of serious fungal diseases. This drug, however, has been reported to have several adverse side effects. The systemic antifungal activity of the A-32390 antibiotic compounds, therefore, is an important aspect of the present invention.

For example, A-32390 factor A is active in vivo against Candida albicans. In tests with mice, A-32390 factor A, when administered by either subcutaneous or intraperitoneal route, gave protection against Candida albicans infections.

In repeated tests, Candida-albicans-infected mice were subsequently treated with four (25 to 50 mg/kg; ip) doses of A-32390 factor A. The life span of these infected but treated mice was 100 percent greater than the life span of similarly infected, but not treated, control mice.

The A-32390 antibiotic compounds are relatively nontoxic. For example, the $LD_0$ (lowest acute dose at which no test animals died) of A-32390 factor A in mice (sc) is greater than 1000 mg/kg.

When used as antifungal agents, the A-32390 antibiotic compounds are administered parenterally. Although it is not essential, the A-32390 antibiotic compounds are more bioavailable when used as antifungal agents if they are formulated together with polyvinylpyrrolidone (PVP) as a dispersion.

A-32390:PVP dispersions are the subject of the copending U.S. patent application of Thakkar titled ANTIBIOTIC A-32390 COMPOSITIONS. Ser. No. 597,115, filed herewith this even date. These A-32390:PVP dispersions contain one part of an A-32390 antibiotic compound together with from one to fifteen parts of a PVP having a molecular weight in the range of from about 10,000 to about 360,000. The dispersions are prepared by dissolving the A-32390 antibiotic compound and the PVP separately, mixing the two solutions and evaporating the resulting solution. It is frequently advantageous to add a small amount of wetting agent such as, for example, polyoxyethylene (20) sorbitan mono-oleate to the A-32390:PVP dispersions. A convenient method of preparing such dispersions is to dissolve the wetting agent, the PVP, and the A-32390 antibiotic compound separately in appropriate solvents; the three solutions are then mixed and evaporated together to give the desired dispersion. A-32390:PVP dispersions provide a more bioavailable form of A-32390 antibiotic compound. As the amount of PVP increases in the dispersion, the amount of A-32390 antibiotic compound required for antifungal effectiveness decreases.

When used as an antifungal agent, the dosage of A-32390 antibiotic compound will also depend on other factors, such as the nature and severity of the particular infection involved. In general, however, satisfactory results can be obtained with daily doses of an A-32390 antibiotic compound between from about 120 to about 600 mg/kg of animal-body weight or with daily doses of an A-32390:PVP dispersion between from about 30 to about 600 mg/kg of animal-body weight. This amount is commonly administered together with a pharmaceutically-acceptable carrier or diluent and may be administered in divided doses such as 2 to 4 times per day.

EXAMPLE 7

Preparation of A-32390:PVP Dispersions

A-32390:PVP dispersions were prepared by dissolving A-32390 factor A in acetone and dissolving PVP having a molecular weight of 40,000 chloroform. The two solutions were mixed. Acetone and/or chloroform were added to the mixture until the solution was clear. The resulting solution was evaporated under vacuum to give a crystalline residue which was ground to a fine powder. A-32390:PVP dispersions prepared in this manner included the following:

| A-32390:PVP Ratio | Amount of A-32390 factor A | Amount of PVP |
|---|---|---|
| 1:1 | 750 mg | 750 mg |
| 1:3 | 500 mg | 1500 mg |
| 1:4 | 500 mg | 2000 mg |
| 1:9 | 500 mg | 4500 mg |

EXAMPLE 8

Preparation of A-32390:PVP Dispersions Containing a Wetting Agent

A-32390:PVP dispersions containing a wetting agent were prepared by dissolving A-32390 factor A in acetone, dissolving PVP having a molecular weight of 40,000 in chloroform, and dissolving 0.01% Tween 80 (Polysorbate 80) in acetone (1 mg/ml). The three solutions were mixed. Acetone and/or chloroform were added to the mixture until the solution was clear. The resulting solution was evaporated under vacuum to give a crystalline residue which was ground to a fine powder. A-32390:PVP dispersions prepared in this manner included the following:

| A-32390:PVP Ratio | Amount of A-32390 factor A | Amount of PVP | Amount of Tween 80 |
|---|---|---|---|
| 1:1 | 750 mg | 750 mg | 150 mcg |
| 1:3 | 500 mg | 1500 mg | 200 mcg |
| 1:4 | 500 mg | 2000 mg | 250 mcg |
| 1:9 | 500 mg | 4500 mg | 500 mcg |

In another aspect of this invention, the A-32390 antibiotic compounds inhibit the enzyme dipamine-$\beta$-hydroxylase and are hypotensive agents. Dopamine-$\beta$-hydroxylase is an enzyme which promotes hydroxylation of dopamine to noradrenaline. Inhibition of dopamine-$\beta$-hydroxylase, therefore, results in a reduction in levels of noradrenaline. In vivo tests with rats demonstrate that doses of from 3 to 200 mg/kg of A-32390 factor A reduce noradrenaline levels in the heart over a period of from 1 to 2 days. The results of some of these tests are summarized in Table III.

TEST METHOD

Male rates (Harlan Industries, Cumberland, Ind.) were used in groups of five. Acacia suspensions containing varying dosage levels of test compound were administered by intraperitoneal injection. After 48 hours the rats were decapitated, and the tissues were removed, rapidly frozen on dry ice and kept frozen until analyzed. Catecholamines were measured fluorometrically, using the method of Chang [Int. J. Neuropharmacol. 3, 643–649 (1964)] for the heart tissue. Internal-standard curves (known amounts of the appropriate catecholamine, in this case noradrenaline, added to tissue homogenates) were used in all cases to convert fluorescence intensity to catecholamine levels. Levels are expressed as mean ± s.e.m.

TABLE III

| Dose A-32390 Factor A (mg/kg) | Noradrenaline Levels | |
|---|---|---|
| | (mcg/gm tissue) | (percent) |
| 0 (control) | 0.87 ± 0.03 | 100 |
| 3 | 0.73 ± 0.04 | 84* |
| 10 | 0.80 ± 0.07 | 92 |
| 32 | 0.62 ± 0.04 | 71** |
| 100 | 0.33 ± 0.07 | 38** |
| *P<0.05 | | |
| **P<0.01 | | |

The A-32390 antibiotic compounds are also useful as hypotensive agents. In representative tests, A-32390 factor A effectively lowers the blood pressure of artificially hypertensive rats.

TEST METHOD

Weanling male rats (Sprague-Dawley) were anesthetized and uninephrectomized. A 25-mg pellet of desoxycorticosterone acetate (DOCA) was implanted in the neck region. The animals were allowed to recover for one week, and then 1 percent saline solution was substituted for the drinking water. The animals were maintained on saline drinking water for three weeks. At this time the rats were hypertensive and maintained high blood pressure without further need for NaCl supplements.

Blood pressure was determined by an indirect route, using the rat tail and an electrosphygmographic technique. To detect any pulse pressure, the animals were warmed at 39° C. for 10 minutes. A control blood pressure was determined for each rat before administration of test compound. Blood pressure was also measured 3, 6, 24 and 48 hours after administration of test compound. Table IV summarizes the results of these tests with rats given varying dosage levels of A-32390 factor A (by the intraperitoneal route)

TABLE IV

| Dose-A-32390 Factor A (ip) | Blood Pressure (mmHg ± s.e.m.)* | | | | |
|---|---|---|---|---|---|
| | Control | Time after Administration (hr) | | | |
| | 0 | 3 | 6 | 24 | 48 |
| 200 mg/kg | 233 ± 5 | 164 ± 9 | 160 ± 10 | 157 ± 8 | 213 ± 11 |
| 200 mg/kg | 192 ± 7 | 162 ± 11 | 138 ± 7 | 128 ± 13 | 132 ± 16 |
| 100 mg/kg | 205 ± 14 | 163 ± 14 | 159 ± 24 | 175 ± 26 | 163 ± 21 |
| 50 mg/kg | 221 ± 13 | 140 ± 12 | 147 ± 10 | 202 ± 17 | 217 ± 8 |
| 25 mg/kg | 218 ± 14 | 154 ± 38 | 152 ± 23 | — | — |

*Mean of four animals

When used either to inhibit the enzyme dopamine-$\beta$-hydroxylase or to lower blood pressure, the A-32390 antibiotic compounds of this invention are normally administered parenterally in the form of a pharmaceutical preparation comprising a therapeutically-active amount of an A-32390 antibiotic compound incorporated into a pharmaceutically-acceptable carrier. Although the dosage amount depends upon factors such as the A-32390 compound used, the manner of administration, and the desired therapeutic effect, the dose generally varies from about 2 to about 30 mg/kg of animal-body weight. A preferred dose range is from about 4 to about 10 mg/kg of animal-body weight.

We claim:

1. The method of producing antibiotic A-32390 factor A which comprises cultivating Pyrenochaeta sp. NRRL 5786 or a mutant thereof which produces antibiotic A-32390 factor A in a culture medium containing assimilable sources of carbohydrate, nitrogen, and inorganic salts under submerged aerobic fermentation conditions until a substantial amount of antibiotic activity is produced.

2. The method of claim 1 which includes the additional step of separating the antibiotic activity produced from said culture medium as an A-32390 antibiotic complex containing antibiotic A-32390 factor A.

3. The method of claim 2 which includes the additional step of isolating antibiotic A-32390 factor A from the separated A-32390 antibiotic complex.

* * * * *